United States Patent [19]

Gross et al.

[11] Patent Number: 4,749,714

[45] Date of Patent: Jun. 7, 1988

[54] NIFEDIPINE ISOSORBIDE 5-MONOITRATE COMBINATION PRODUCT

[75] Inventors: Rainer Gross, Wuppertal; Matthias Schramm, Cologne, both of Fed. Rep. of Germany

[73] Assignee: Bayer Aktiengesellschaft, Leverkusen, Fed. Rep. of Germany

[21] Appl. No.: 98,334

[22] Filed: Sep. 18, 1987

Related U.S. Application Data

[63] Continuation-in-part of Ser. No. 875,138, Jun. 17, 1986, abandoned.

[30] Foreign Application Priority Data

Jul. 2, 1985 [DE] Fed. Rep. of Germany ....... 3523544

[51] Int. Cl.$^4$ ...................... A61K 31/34; A61K 31/44
[52] U.S. Cl. ..................................... 514/356; 514/470
[58] Field of Search ................................ 514/356, 470

[56] References Cited

FOREIGN PATENT DOCUMENTS 1173862 12/1969 United Kingdom .

OTHER PUBLICATIONS

The Merck Index (1983) p. 751.
Table; article of U. Borchard et al. in Med. Klin. 1985, pp. 21–23.

*Primary Examiner*—Allen J. Robinson
*Attorney, Agent, or Firm*—Sprung Horn Kramer & Woods

[57] ABSTRACT

A solid medicament formulation which can be administered orally comprising 5 to 30 mg of nifedipine and 10 to 40 mg of isosorbide 5-mononitrate. Oral administration of such cardioactive formulation reduces the time tolerance to the isosorbide 5-mononitrate alone.

5 Claims, No Drawings

NIFEDIPINE ISOSORBIDE 5-MONOITRATE COMBINATION PRODUCT

This is a continuation-in-part of Application Ser. No. 875,138, filed June 17, 1986, now abandoned.

The present invention relates to a solid combination product containing nifedipine and isosorbide 5-mononitrate, which can be used for the chronic treatment of heart diseases, in particular of diseases of the coronaries and of the myocardium in humans and other animals.

The compound nifedipine is known (British Pat. No. 1,173,862) and is successfully used for the treatment of hypertension, of coronary heart disease and of cardiac insufficiency.

The known compound isosorbide 5-mononitrate (called IS-5-MN in the subsequent text) likewise has a vasodilator action, there being a preferential action on the veins on treatment of heart diseases. On chronic treatment of heart diseases with nitro products there is frequently an undesired development of tolerance, which makes an increase in the dosage necessary or no longer shows an adequate therapeutic action.

The invention relates to solid medicament formulations which can be administered orally for use for the chronic control of heart diseases, in particular diseases of the coronaries and of the myocardium, containing 5 to 30 mg of the active compound nifedipine and 10 to 40 mg of the active compound isosorbide 5-mononitrate and, where appropriate, customary auxiliaries and vehicles.

Particular interest attaches to those combination products which contain 10 to 30 mg of nifedipine and 10 to 30 mg of isosorbide 5-mononitrate. Such combination will be effective taken two or three times daily by an adult human weighing 150 pounds.

Surprisingly, when the combination of nifedipine and IS-5-MN is used there is prevention of the development of tolerance to the nitrate component, which can also be demonstrated in experiments on isolated tissues. Thus, for example, the development of tolerance to nitrates can be demonstrated by determination of their action on the serotonin-induced contraction of pulmonary veins (U. Borchard et al., Med. Klin., Special Issue 1 (1985), 21–23).

If, in these experiments, the effect of the substance immediately after administration of the substance is set equal to 100%, then the decrease in this effect with time is a measure of the development of tolerance. The following figures emerged after five hours:

| Concentration (g/ml) IS-5-MN | nifedipine | Loss of effect after 5 hours (%) |
|---|---|---|
| $10^{-4}$ | 0 | 42 |
| $3 \times 10^{-4}$ | 0 | 48 |
| 0 | $10^{-6}$ | 0 |
| 0 | $3 \times 10^{-6}$ | 0 |
| $10^{-4}$ | $10^{-6}$ | 7 |

This unexpected finding is a crucial advantage especially for the chronic treatment, which is necessary, of the syndromes mentioned.

Furthermore, the present invention makes it possible for those skilled in the art to achieve the same therapeutic effect with a considerably reduced dosage of the individual components of the active compounds. This means that adverse side effects are also reduced. This is a great advantage especially on chronic treatment.

The examples which follow illustrate specific embodiments of the combination products according to the invention, without having a restrictive action.

PREPARATION EXAMPLES

Example 1

10 g of nifedipine (microfine) are mixed with 80 g of a trituration of IS-5-MN in lactose (25% strength), 41.4 g of corn starch, 15 g of lactose and 20 g of Avicel, and then granulated with a solution of 0.8 g of sodium lauryl sulphate in 12 g of polyvinylpyrrolidone (PVP 25). The granules are dried, screened and mixed with 0.8 g of magnesium stearate. Tablets with a mean tablet weight of 180 mg are compressed from this mixture, or the mixture is dispensed into hard gelatin capsules with a capsule capacity of 180 mg.

Example 2

15 g of nifedipine are mixed with 20 g of a trituration of IS-5-MN in lactose (50% strength), 15 g of microcrystalline cellulose, 30 g of lactose and 16 g of corn starch, and are granulated with a paste of 4.25 g of maize starch. The resulting granules 1 are dispensed into hard gelatin capsules or compressed to form tablets which contain 5, 10 or 20 mg of nifedipine.

Example 3

Granules 1 according to Example 2 are mixed with the following granules 2, which contain nifedipine in the form of a coprecipitate, with the addition of 4% of crosslinked polyvinylpyrrolidone and 1% of magnesium stearate, and are compressed to form tablets.

Preparation of granules 2:
10 g of nifedipine and 40 g of PVP 25 are dissolved in 60 g of acetone. This solution is granulated with a mixture of 105 g of microcrystalline cellulose, 20 g of corn starch and 10 g of crosslinked polyvinylpyrrolidone, and is dried in vacuo before being mixed together with granules 1.

Example 4

(Preparation of granules 1):
20 g of nifedipine are mixed with 40 g of a trituration of IS-5-MN in lactose (25% strength), 10 g of microcrystalline cellulose and 20 g of corn starch, and are granulated with a paste of 6 g of corn starch. These granules 1 are then mixed with the coprecipitate granules of Example 3 and compressed to form tablets.

It will be understood that the specification and examples are illustrative but not limitative of the present invention and that other embodiments within the spirit and scope of the invention will suggest themselves to those skilled in the art.

We claim:

1. A solid medicament formulation for the treatment of diseases of the coronaries and of the myocardium and which can be administered orally comprising 5 to 30 mg of nifedipine and 10 to 40 mg of isosorbide 5-mononitrate.

2. A medicament formulation according to claim 1, comprising 10 to 30 mg of nifedipine and 10 to 30 mg of isosorbide 5-mononitrate.

3. A medicament formulation according to claim 1, wherein 5 to 10 mg of the total content of nifedipine in each formulation is present in the form of a coprecipitate.

4. A formulation according to claim 1, in the form of a tablet or capsule.

5. A method of treating a patient having a disorder of the coronaries or myocardium which comprises orally administering to such patient an amount effective therefor of a composition according to claim 1.

* * * * *